June 15, 1943. A. DICKSON, JR Plant Pat. 590
ROSE PLANT
Filed Dec. 31, 1942
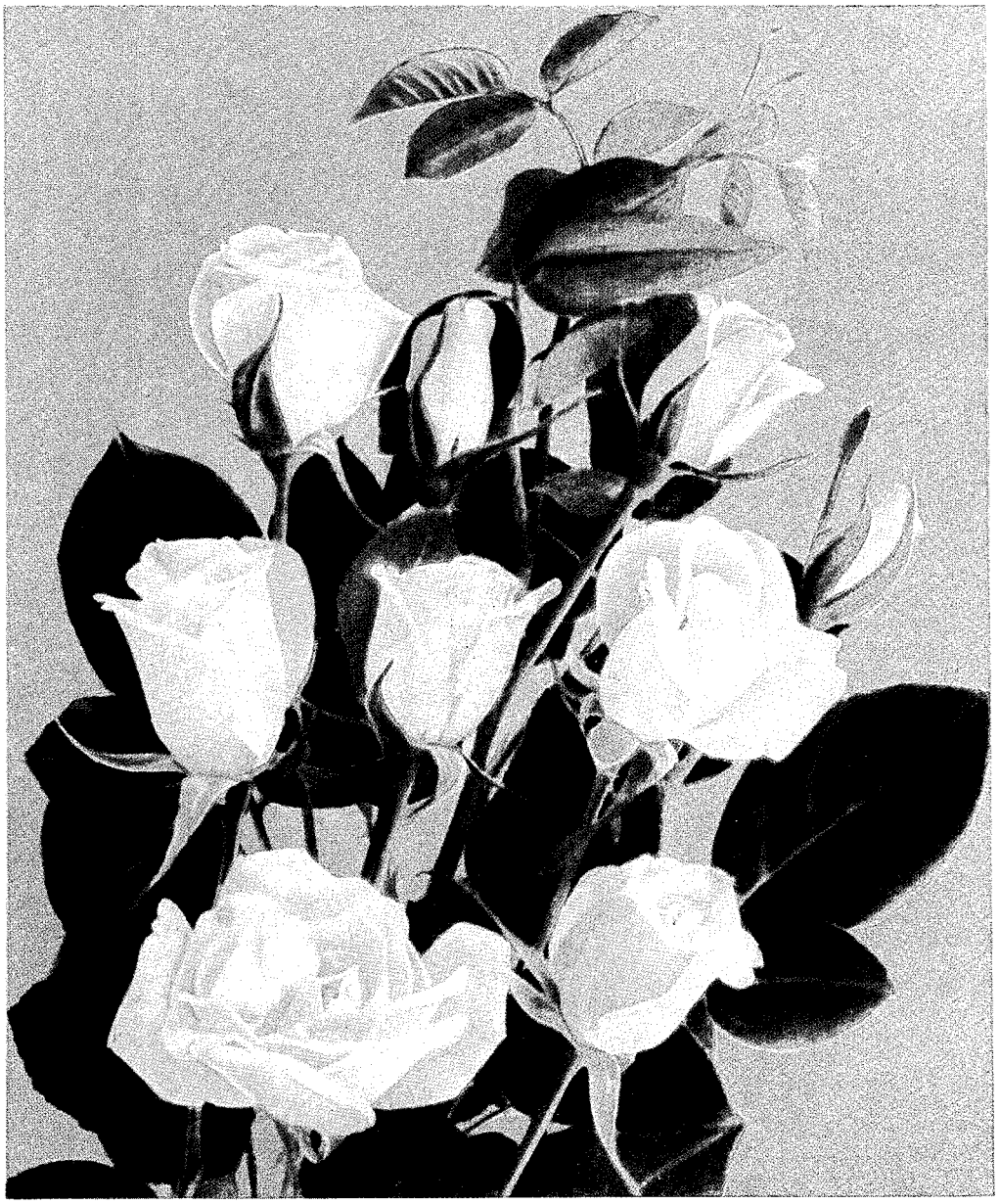
Inventor
A. Dickson, Jr.
By Robbins & Robbins
Attorneys Patented June 15, 1943

UNITED STATES PATENT OFFICE

590

ROSE PLANT

Alexander Dickson, Jr., Newtonards, Belfast, Ireland, assignor to Jackson & Perkins Company, Newark, N. Y.

Application December 31, 1942, Serial No. 470,793

1 Claim. (Cl. 47—61)

The present invention relates to a new and distinct variety of rose plant of the Floribunda class, originated by crossing an unnamed Dickson seedling and the well-known "Lord Lonsdale" variety.

The object in view in producing the present variety was to obtain the free flowering characteristic and vigor of the bush of the Dickson seedling in a plant retaining the deep rich color of the "Lord Lonsdale" variety. Not only was this objective realized in this new variety, but other very desirable characteristics were obtained, with the result that the new rose produces great quantities of clusters and groups of flowers, especially suited for corsage and basket work and other special arrangements.

The new rose is distinctive because, instead of the small bush, of the "Lord Lonsdale" type, a large one is established particularly suitable for the purpose of greenhouse cut flowers to be used in the Sweetheart class of roses.

This new rose is also distinctive for its continuous blooming habit and the production of Light Cadmium Yellow buds which are strikingly set off by the Dark Cress Green foliage.

Asexual reproduction of this new variety shows the foregoing characteristics come true to form and are established.

The following is a detailed description of the new variety, all color terminology being in accord with Ridgway's Color Standard:

Parentage: Seedling.
- *Seed parent.*—Dickson seedling.
- *Pollen parent.*—"Lord Lonsdale."

Classification:
- *Botanic.*—Hybrid Tea Floribunda Cross.
- *Commercial.*—Floribunda.

*Flower*

(Observations made in the greenhouse of Jackson & Perkins Company, Newark, New York, in October, 1942.)

Blooming habit:
- *Recurrent.*—Continuous.

Bud:
- *Size.*—Small to medium.
- *Form.*—Pointed. Is not affected by wet or hot weather.
- *Color.*—When sepals first divide—Light Cadmium, Plate 4. When petals begin to unfurl—Apricot Yellow, Plate 4. When half blown—Inside of petals, Apricot Yellow, Plate 4. Reverse of petals—Lower half, Apricot Yellow, Plate 4; upper half, Empire Yellow, Plate 4.
- *Sepals.*—Serrated, branched, "hood" above bud. Curl back when petals begin to unfurl. *Color*—inside, Pale Tiber Green, Plate 18; outside, Absinthe Green, Plate 31.
- *Calyx.*—*Shape*—funnel. *Size*—slender. *Aspect*—smooth. *Color*—Lettuce Green, Plate 5. *Odor when rubbed*—None.
- *Peduncle.*—*Length*—medium. *Aspect*—smooth. *Color*—Lettuce Green, Plate 5. *Strength*—erect; slender.
- *Opening.*—Bud opens well. Is not affected by adverse conditions.

Bloom:
- *Size.*—Medium. Average size when fully expanded, 3¾".
- *Borne.*—Several together and in clusters. In clusters—irregular.
- *Stems.*—Medium length; strong.
- *Form.*—When first open—high center. Permanance—flattens.
- *Petalage.*—Double (full but open center). Number of petals under normal conditions—30–35.
- *Color.*—Center of flower—Light Orange Yellow, Plate 3. Outer petals—Pinard Yellow, Plate 4, with lower half of petal overcast very lightly with Empire Yellow, Plate 4. Base of petals (aiglet)—Lemon Chrome, Plate 4. Inside of petals—Between Empire Yellow, Plate 4, and Pinard Yellow, Plate 4; upper edges fading lighter to Baryta Yellow, Plate 4. Reverse of petals—Between Pinard Yellow, Plate 4, and Empire Yellow, Plate 4. General tonality from a distance—Empire Yellow, Plate 4.
- *Discoloration.*—General tonality at end of first day—Empire Yellow, Plate 4. Second day—Empire Yellow, Plate 4. Third day—Between Empire Yellow, Plate 4, and Pinard Yellow, Plate 4.

Petals:
- *Texture.*—Leathery. Is not affected by wet or hot weather.
- *Appearance.*—Inside, satiny; outside, shiny.
- *Form.*—Oval.
- *Arrangement.*—Imbricated (regularly arranged shinglelike). Petaloids in center—few; small.
- *Persistence.*—Drop off cleanly.
- *Fragrance.*—Strong. *Nature*—Sweet fruity (Russet apple).
- *Lasting quality.*—On the plant and as cut flower—long.

Genital organs:

*Stamens, Anthers.*—Medium size; few. *Color*—Apricot Yellow, Plate 4. *Arrangement*—Regular around styles.

*Stamens, filaments (threads).*—Medium length. *Color*—Lemon Chrome, Plate 4.

*Pollen.*—Apricot Yellow, Plate 4.

*Styles.*—Bunched, uneven length. Medium long and thin.

*Stigmas.*—Pinard Yellow, Plate 4.

*Ovaries.*—All enclosed in calyx.

*Plant*

Form: Bush.

Growth: Vigorous; upright.

Foliage: 5 leaflets.

*Size.*—Large.

*Quantity.*—Normal.

*Color.*—*New foliage*—Upper side, Oil Green, Plate 5; edges Mahogany Red, Plate 2. Under side, Yellowish Oil Green, Plate 5, overlaid with Mahogany Red, Plate 2. *Old foliage*—Upper side, Dark Cress Green, Plate 31. Under side, Light Cress Green, Plate 31.

*Shape.*—Oval pointed.

*Texture.*—Upper side—glossy. Under side—rough. Ribs and veins—ordinary.

*Edge.*—Serrated (saw toothed).

*Serration.*—Single; small.

*Rachis.*—Yellowish Oil Green, Plate 5. Under side—smooth.

*Stipules.*—Medium length; serrated.

*Disease resistance.*—Resistant.

Wood:

*New wood.*—*Color*—Jade Green, Plate 31. *Bark*—smooth.

*Old wood.*—*Color*—Cress Green, Plate 31. *Bark*—smooth.

Thorns (thorns are divided into thorns, prickles and short needles):

*Thorns.*—*Quantity*—on main stalks from base and on laterals from stalk—few. *Form*—narrow base; medium length; hooked downward. *Color when young*—Madder Brown, Plate 13. *Position*—irregular.

*Prickles.*—*Quantity*—on main stalks and on laterals—none.

*Short needles.*—*Quantity*—on main stalks and on laterals—none.

I claim:

A new and distinct variety of rose plant, of the Hybrid Tea Floribunda type, characterized as to novelty by its vigor of bush growth to large size and free flowering habit, continuously producing buds of deep rich golden yellow color, similar to "Lord Lonsdale," in great quantities of clusters and groups with dark green foliage settings, suited particularly for greenhouse cut flowers for corsage and basket work, substantially as shown and described.

ALEXANDER DICKSON, JR.